(12) United States Patent
Hell

(10) Patent No.: US 9,719,928 B2
(45) Date of Patent: Aug. 1, 2017

(54) HIGH-RESOLUTION FLUORESCENCE MICROSCOPY USING A STRUCTURED BEAM OF EXCITATION LIGHT

(71) Applicant: Max-Planck-Gesellschaft zur Foerderung der Wissenschaften e.V., Munich (DE)

(72) Inventor: Stefan W. Hell, Goettingen (DE)

(73) Assignee: MAX-PLANCK-GESELLSCHAFT ZUR FOERDERUNG DER WISSENSCHAFTEN E.V., Munich (DE)

( * ) Notice: Subject to any disclaimer, the term of this patent is extended or adjusted under 35 U.S.C. 154(b) by 0 days.

(21) Appl. No.: 15/189,300

(22) Filed: Jun. 22, 2016

(65) Prior Publication Data

US 2016/0305884 A1  Oct. 20, 2016

Related U.S. Application Data

(63) Continuation of application No. PCT/EP2014/077527, filed on Dec. 12, 2014.

(30) Foreign Application Priority Data

Dec. 23, 2013  (DE) .................. 10 2013 114 860

(51) Int. Cl.
*G01N 21/64* (2006.01)
*G01B 11/14* (2006.01)
(Continued)

(52) U.S. Cl.
CPC ......... *G01N 21/6458* (2013.01); *G01B 11/14* (2013.01); *G02B 21/008* (2013.01);
(Continued)

(58) Field of Classification Search
CPC ............ G01N 21/6458; G02B 21/0032; G02B 21/0076; G02B 21/008; G01B 11/14
See application file for complete search history.

(56) References Cited

U.S. PATENT DOCUMENTS 6,958,470 B2  10/2005  Hoffmann
7,485,875 B2  2/2009  Wolleschensky
(Continued)

FOREIGN PATENT DOCUMENTS

DE    101 05 391 A1    8/2002
DE    103 25 459 A1    11/2004
(Continued)

OTHER PUBLICATIONS

Aquino et al.: "Two-color nanoscopy of three-dimensional volumes by 4Pi detection of stochastically switched fluorophores." Nature Meth. 8, 353-359 (2011).
(Continued)

*Primary Examiner* — David Porta
*Assistant Examiner* — Mindy Vu
(74) *Attorney, Agent, or Firm* — Thomas | Horstemeyer, LLP

(57) ABSTRACT

In order to determine the locations of individual fluorescent molecules in a sample, which keep a minimum distance with regard to each other, the individual molecules are excited for emission of fluorescence light by means of excitation light. The fluorescence light is registered for different positions of a zero point of an intensity distribution of the excitation light. The distance between these positions is at least half the minimum distance of the fluorescent molecules. The locations of the fluorescent molecules are derived from the course of the intensity of the fluorescence light over the positions of the zero point of the excitation light.

26 Claims, 6 Drawing Sheets

(51) Int. Cl.
*G02B 21/00* (2006.01)
*G02B 21/16* (2006.01)
*G02B 21/36* (2006.01)
*G02B 27/58* (2006.01)

(52) U.S. Cl.
CPC ..... *G02B 21/0032* (2013.01); *G02B 21/0076* (2013.01); *G02B 21/16* (2013.01); *G02B 21/367* (2013.01); *G02B 27/58* (2013.01); *G01N 2201/068* (2013.01); *G01N 2201/10* (2013.01)

(56) References Cited

U.S. PATENT DOCUMENTS

| | | |
|---|---|---|
| 7,539,115 B2 | 5/2009 | Hell |
| 7,679,741 B2 | 3/2010 | Dyba |
| 7,709,809 B2 | 5/2010 | Kempe |
| 7,903,247 B2 | 3/2011 | Dyba |
| 8,174,692 B2 | 5/2012 | Hell et al. |
| 8,207,510 B2 | 6/2012 | Kempe et al. |
| 8,362,448 B2 | 1/2013 | Wolleschensky |
| 8,704,196 B2 | 4/2014 | Wolleschensky |
| 9,024,279 B2 | 5/2015 | Hell |
| 9,291,562 B2 | 3/2016 | Hell |
| 2006/0275182 A1* | 12/2006 | Hudson ............ B01L 3/5085 422/400 |
| 2007/0206278 A1 | 9/2007 | Dyba et al. |
| 2009/0139908 A1* | 6/2009 | Zhou ............... B03C 1/033 209/225 |
| 2012/0319007 A1* | 12/2012 | Kempe ............ G02B 21/16 250/459.1 |

FOREIGN PATENT DOCUMENTS

| | | |
|---|---|---|
| DE | 10 2005 034 443 A1 | 2/2007 |
| DE | 10 2006 009 831 A1 | 9/2007 |
| DE | 10 2006 009 833 A1 | 9/2007 |
| DE | 10 2006 026 204 A1 | 12/2007 |
| DE | 10 2006 047 912 A1 | 4/2008 |
| DE | 10 2008 009 216 A1 | 8/2009 |
| DE | 10 2008 054 317 A1 | 5/2010 |
| DE | 10 2009 008 646 A1 | 8/2010 |
| DE | 10 2010 028 138 A1 | 10/2011 |
| DE | 10 2011 055 367 A1 | 5/2013 |
| WO | 2006-127692 A2 | 11/2006 |
| WO | 2011/076458 A1 | 6/2011 |
| WO | 2012/171999 A1 | 12/2012 |

OTHER PUBLICATIONS

Engelhardt, J. et al.: "Molecular orientation affects localization accuracy in superresolution far-field fluorescence microscopy." Nano Lett. 2011, Jan. 12, 2011, 11 (1) : 209-13.
Gustafsson, M.G.L. "Nonlinear structured-illumination microscopy: Wide-field fluorescence imaging with theoretically unlimited resolution." Proc. Natl. Acad. Sci. USA 102, 13081-13086 (2005).
Chmyrov, Andriy et al.: "Nanoscopy with more than 100,000 doughnuts", Nature Meth., vol. 10, No. 8 Jul. 7, 2013, pp. 737-740.
Schmidt, R. et al.: Spherical nanosized focal spot unravels the interior of cells, Nature Meth. 5, 539-544 (2008).
International Preliminary Examination Report in co-pending, related PCT Application No. PCT/EP2014/077527, mailed Jun. 28, 2016.

* cited by examiner

HIGH-RESOLUTION FLUORESCENCE MICROSCOPY USING A STRUCTURED BEAM OF EXCITATION LIGHT

CROSS REFERENCE TO RELATED APPLICATIONS

The present application is a continuation to International Patent Application PCT/EP2014/077527 filed Dec. 12, 2014 and entitled "High-Resolution Fluorescence Microscopy with a Structured Excitation Beam", and claims priority to German Patent Application DE 10 2013 114 860.3 filed Dec. 23, 2013 and entitled "Hochauflösende Fluoreszenz-Mikroskopie mit einem strukturierten Anregungsstrahl".

FIELD OF THE INVENTION

The present invention relates to a method of determining the locations of individual molecules of a substance with in a sample and to an apparatus for carrying out this method. The method and the apparatus particularly serve for the purpose of high spatial resolution imaging a distribution of the molecules of the substance within the sample or a structure of the sample marked with the substance.

BACKGROUND OF THE INVENTION

There are two different general ways of determining the locations of molecules in a sample, which emit fluorescence light. According to the first general way, the locations are deduced from the spatial distribution of the fluorescence light registered by means of a light sensor array. According to the second general way, the locations of the molecules are assigned to spatially delimited excitation areas in which the molecules are locally excited for the emission of the fluorescence light and for which the fluorescence light emitted by the molecules is registered separately.

According to the first general way in which the fluorescence light emitted by the substance is registered by means of a light sensor array onto which the sample is imaged by means of an objective lens, the spatial resolution or accuracy achievable in imaging the distribution of the molecules of the substance in the sample or in imaging a structure of the sample marked with the substance is delimited by the so-called Abbe diffraction limit. According to the Abbe diffraction limit, one may determine a location of a molecule in a sample emitting an individual photon which has been registered at a certain location of the light sensor array only at a spatial uncertainty in the region of $\lambda/2n \sin \alpha$, wherein $\lambda$ is the wavelength of the fluorescence light, n is the refraction index of the optical material arranged between the sample and the objective lens, and $\alpha$ is half the aperture angle of the objective lens.

If, however, the fluorescence light registered at the light sensor array may be assigned to a single fluorescing molecule in the sample and if the single fluorescing molecule emits a higher number of photons, the location of the molecule can be determined at a spatial accuracy beyond the diffraction limit. For this purpose, the center of the distribution of the positions of the light is sensor array is determined at which the individual photons are registered, and the location of the emitting molecule is deduced therefrom. The spatial resolution achieved by this method which is called localization increases with $\sqrt{n}$, wherein n is the number of the photons emitted by the molecule and registered by the light sensor array.

If a molecule emits fluorescence light in a directional spatial distribution, this results in a spatial error in determining the location of the molecule from the intensity distribution of the fluorescence light over a light sensor array by means of localization. This spatial error depends on the orientation of the molecule within the sample. A directional spatial distribution of the emitted fluorescence light is, for example, displayed by molecules whose rotation diffusion times are longer than the lifetimes of their excited state out of which they emit the fluorescence light. (See Engelhardt, J. et al., Molecular orientation affects localization accuracy in superresolution far-field fluorescence microscopy, Nano Lett. 2011, Jan. 12; 11(1): 209-13.)

International Patent Application publication WO 2006/127692 discloses to mark a structure of interest in a sample with molecules of a substance which are in a non-fluorescent starting state but which, by means of adjusting light, can be switched into a fluorescent state. Thus, by means of the adjusting light, a small proportion of the molecules can be brought into the fluorescent state in which the distances to nearest neighboring molecules in the fluorescent state are greater than the diffraction limit. With a following application of excitation light, only the molecules in the fluorescent state emit fluorescence light. Thus, the fluorescence light from the individual molecules in the fluorescent state can be registered separately, and the locations of the individual molecules may be determined by means of localization at a spatial accuracy beyond the diffraction limit despite the high absolute concentration of the molecules in the substance. Imaging the distribution of the molecules of he substance in the sample is achieved successively in that the steps of transferring a small proportion of the molecules into the fluorescent state, of exciting these molecules for the emission of fluorescence light, and of registering the fluorescence light by means of a light sensor array are repeated and, thus, for statistical reasons, executed for different portions of the molecules of the substance in the sample.

WO 2006/127692 also describes that activating a portion of the molecules of the substance into a fluorescent state may be combined with other optical imaging methods. For example, by means of an intensity distribution of the excitation light comprising maxima delimited by minima, the molecules of the substance may only be excited for the emission of fluorescence light in certain planes or other spatial subunits of the sample.

The method known from WO 2006/127692 for determining the position of each molecule of the substance at a spatial accuracy beyond the diffraction limit requires a number of photons from the molecule, and this number increases with the desired spatial accuracy. Further, the method makes great demands on the molecules to enable that only a small proportion of the molecules can be switched into the fluorescent state, the distances between the molecules switched into the fluorescent state being greater than the diffraction limit. Typically, the molecules are photochromic fluorophores or proteins which can be switched between two conformation states one of which being fluorescent.

The method known from WO 2006/127692 is also known as PALM, i.e. Photo-Activated Localization Microscopy. A similar method known as STORM (Stochastic Optical Reconstruction Microscopy) basically has the same advantages and drawbacks.

U.S. Pat. No. 8,174,692 B2 discloses that even standard dyes which are not switchable but have a fluorescent starting state, which are arranged at smaller distances than the diffraction limit, and which may not be switched between two conformation states, only one of which being fluorescent, can be used as a substance to determine the location of individual molecules of the substance by means of localization. Here, the sample is subjected to excitation light, which, at a certain transition probability, transfers the molecules into a relatively long-living electronic dark state, at such a high intensity that the molecules still being in the fluorescent starting state are arranged at distances beyond the diffraction limit.

By means of the excitation light, the molecules presently being in their fluorescent state are excited for the emission of fluorescence light which is registered with spatial resolution by means of a light sensor array. In this way, successively, different molecules of the substance are localized, as the molecules from which photons have already been registered get into the dark state, whereas other molecules, at a certain transition probability, return into the fluorescent state. This known method can be carried out continuously, i.e. frames may be continuously read out of the light sensor array whereas the sample is subjected to a high intensity of the excitation light which essentially keeps the substance in its dark state and only excites isolated molecules for the emission of fluorescence light.

The method known from U.S. Pat. No. 8,174,692 B2 is also designated as GSDIM (Ground State Depletion Individual Molecule Return Microscopy).

The high spatial resolution in determining the locations of isolated or individual fluorescent molecules by means of localization is only achieved in the x- and y-direction running orthogonal to the optical axis but not in the z-direction of the optical axis of the objective lens by which the respective sample is imaged onto the light sensor array. However, from Aquino, D. et al., Two-color nanoscopy of three-dimensional volumes by 4Pi detection of stochastically switched fluorophores, Nature Meth. 8,353-359 (2011) it is known that the locations of the individual fluorescence molecules in a PALM-, STORM-, or GSDIM-method can be determined by means of a 4Pi method with two facing objectives aligned in the z-direction of the optical axis by scanning the sample with an x-y-measurement plane.

When the locations of molecules emitting fluorescence light are equated with the position of their spatially limited excitation for emission of fluorescence light, the respective sample being scanned or rasterized with the locations of their spatially limited excitation, this is called scanning fluorescence light microscopy. With regard to the spatial resolution or accuracy achieved in scanning fluorescence light microscopy, the Abbe diffraction limit also normally applies, here at the wavelength of the excitation light. However, some methods are known by which the spatial accuracy in scanning fluorescence light microscopy can be enhanced beyond the diffraction limit by means of reducing the effective spatial area of the excitation of the molecules of the substance for emission of fluorescence light.

In scanning fluorescence light microscopy, the registration of any photons is sufficient to determine whether molecules of the substance emitting fluorescence light are located in the present area of the excitation. The number of the photons registered is only used for determining the local concentration of the molecules of the substance in the present area of the excitation.

In STED (Stimulated Emission Depletion) fluorescence light microscopy, directly after molecules of a substance marking a structure of a sample have been excited by means of excitation light, the excitation is removed in surroundings of a measurement point of interest by means of directed emission. This directed emission is stimulated by means of STED light and inhibits the emission of fluorescence light by the molecules so that the fluorescence light may only come out of that area of the sample in which the excitation has not been removed. The area in which the excitation has not been removed can be kept very small in that it is defined by means of a zero point or null of the intensity distribution of the STED light and in that the absolute intensity of the STED light is adjusted so high that it completely removes the excitation of the molecules even very close to the zero point.

Instead of removing a previously effected excitation of the molecules in parts of the sample, light having an intensity distribution comprising a zero point may also be used for switching the molecules of the substance into a non-fluorescent conformation state, like it is done in RESOLFT fluorescence light microscopy, or into an electronic dark state, like it is done in GSD (Ground State Depletion) fluorescence light microscopy.

U.S. Pat. No. 7,485,875 B2, corresponding to DE 10 2005 034 443 A1, discloses a GSD method using light of one wavelength only. Up to a certain intensity, this light excites the substance primarily for the emission of fluorescence light. Above this intensity, the light transfers the molecules of the substance essentially completely into a dark state. In that an intensity distribution, at which the light is applied to the sample, has a local minimum lower than the certain intensity described, the area in which the molecules of the substance are effectively excited for the emission of fluorescence light is spatially delimited.

International Patent Application publication WO 2012/171999 teaches to scan a sample with a beam of excitation light surrounded by an intensity distribution of STED light having a minimum at the focus point of the excitation light so quickly that, in each of several scanning passages, the fluorescence light registered consists of individual photons emitted by individual molecules. The locations of the molecules are equated with the positions of the focus point of the beam of excitation light at which the photons of the fluorescence light has been registered.

U.S. Pat. No. 9,291,562 B2, corresponding to DE 10 2011 055 367 A1, discloses a method of tracking a single fluorescent molecule, which, by means of excitation light, is caused for the emission of fluorescence light, the fluorescence light being registered. The excitation light is applied to the sample with an intensity distribution comprising a local minimum, and the molecule moving within the sample is tracked with the local minimum. For this purpose, the intensity distribution of the excitation light is shifted moved with regard to the sample such that an intensity of the fluorescence light emitted by the particle remains minimal. The minimal intensity of the fluorescence light emitted by the particle is that rate at which individual photons are emitted by the respective molecule if the molecule is located in the minimum of the intensity distribution of the excitation light. This minimum may be a zero point or null of the intensity distribution of the excitation light.

U.S. Pat. No. 9,024,279 B2, corresponding to DE 10 2010 028 138 A1, discloses a method of determining the distribution of a substance in a measurement area by means of scanning with a measurement front. Over a depth of the measurement front which is shorter than the diffraction limit at the wavelength of an optical signal, the intensity of the optical signal increases in such a way that a proportion of the substance in a measurement state at first increases from non-existing and then drops down to non-existing again. The measurement front is shifted or moved over the measurement area in opposite direction to the increase of the intensity of the optical signal. The measurement signal emitted out of the area of the measurement front is registered and assigned to the respective position of the measurement front within the measurement area.

In so-called SSIM (Saturated Structured Illumination Microscopy, see Gustafsson, M. G. L., *Proc. Natl. Acad. Sci. USA* 102, 13081-13086 (2005)), a sample is scanned in different directions with an intensity distribution of excitation light which has a line-shaped zero point and such high intensities outside the zero point that a saturation of the intensity of the fluorescence light by excited molecules of a fluorescent substance within the sample is achieved. Fluorescence light from the sample registered during scanning varies due to the fact that molecules of the fluorescent substance which are presently in the area of the zero point do not contribute to the fluorescence light. This fluorescence light is evaluated with regard to spatial frequencies which develop in scanning in the various directions and from which an image of the distribution of the fluorescent molecules in the sample may then be reconstructed.

SSIM does not make use of a distribution of the fluorescent molecules in the sample in which an average distance of the molecules is higher than the diffraction limit at the wavelength of the excitation light or the fluorescence light. SSIM may only be carried out with fluorescent molecules which can be excited up to the saturation of the intensity of the fluorescence light emitted by them without transferring them into a dark state. The image of the distribution of the molecules of the fluorescent substance in the sample is only achieved indirectly. Positions of individual fluorescent molecules in the sample are not determined.

There still is a need of a method and an apparatus for determining the locations of individual molecules of a substance in a sample by which a high spatial resolution image of a distribution of the molecules of the substance in the sample can be produced by evaluating the fluorescence light obtained from the individual molecules, which may additionally be used for determining the locations of individual molecules by means of localization.

SUMMARY OF THE INVENTION

The present invention relates to a method of determining the locations of individual molecules of a substance in a sample, wherein the individual molecules of the substance are in a fluorescent state in which they are excitable for emission of fluorescence light by means of excitation light. The method comprises forming an intensity distribution of the excitation light comprising at least one local minimum of the intensity of the excitation light; exciting the individual molecules of the substance in the fluorescent state for the emission of the fluorescence light by means of the excitation light; registering an intensity of the fluorescence light emitted by the excited individual molecules of the substance in the fluorescent state for different positions of the at least one minimum in an area of interest of the sample; and deducing the locations of the individual molecules of the substance in the fluorescent state from a course of the registered intensity of the fluorescence light over the positions of the at least one minimum in the area of interest of the sample. Distances between the individual molecules of the substance in the fluorescent state keep a minimum value $d=\lambda/(2n \sin \alpha \sqrt{(1+I/I_s)})$ in the area of interest of the sample, wherein $\lambda$ is a wavelength of the excitation light, n is the refraction index of an optical material in which the intensity distribution of the excitation light with the at least one minimum is formed, $\alpha$ is half an aperture angle of an optical arrangement by which the excitation light is directed onto the sample, I is a maximum intensity of the excitation light within the sample, and $I_s$ is a substance-dependent fluorescence excitation saturation intensity of the excitation light. The intensity of the fluorescence light emitted by one of the individual molecules at a location of the local minimum of the intensity distribution of the excitation light is at maximum half as great as the intensity of the fluorescence light emitted by the one of the individual molecules at a location of the maximum intensity of the excitation light within the sample; and increments between nearest neighboring positions of the at least one minimum within the sample, in which the fluorescence light from the excited individual molecules of the substance in the fluorescent state is registered, are not greater than half the minimum value d.

The present invention also relates to an apparatus for determining the locations of individual molecules of a substance in a sample, wherein the individual molecules of the substance are in a fluorescent state in which they are excitable for emission of fluorescence light by means of excitation light. The apparatus comprises an excitation light source configured to provide the excitation light, by which the molecules of the substance in the fluorescent state are excited for the emission of the fluorescence light, and by which the molecules of the substance are transferred out of their fluorescent state into a non-fluorescent state. Further, the apparatus comprises light shaping optics configured to form an intensity distribution of the excitation light within the sample which comprises at least one local minimum, wherein the intensity of the fluorescence light emitted by one of the individual molecules at a location of the local minimum of the intensity distribution of the excitation light is at maximum half as high as the intensity of the fluorescence light emitted by the one of the individual molecules at a location of the maximum intensity of the excitation light within the sample. Further, the apparatus comprises an optical arrangement configured to project the excitation light into the sample; a scanning device configured to position the at least one minimum at different positions within the sample; and a detector device configured to register the fluorescence light emitted by the molecules of the substance in the fluorescent state which have been excited by means of the fluorescence light, wherein the detector device is configured to register the fluorescence light emitted out of a registration area including the at least one minimum separately from fluorescence light emitted out of other areas of the sample. Increments between nearest neighboring positions of the at least one minimum, in which the detector device registers the fluorescence light emitted out of the registration area, are not greater than $\lambda/(4n \sin \alpha \sqrt{(1+I/I_s)})$, wherein $\lambda$ is a wavelength of the excitation light, n is the refraction index of an optical material in which the intensity distribution of the excitation light with the at least one minimum is formed by means of the light shaping optics, $\alpha$ is half the aperture angle of the optical arrangement by which the excitation light is directed into the sample. I is the maximum intensity of the excitation light within the sample, and $I_s$ is a substance-dependent fluorescence excitation saturation intensity of the excitation light.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
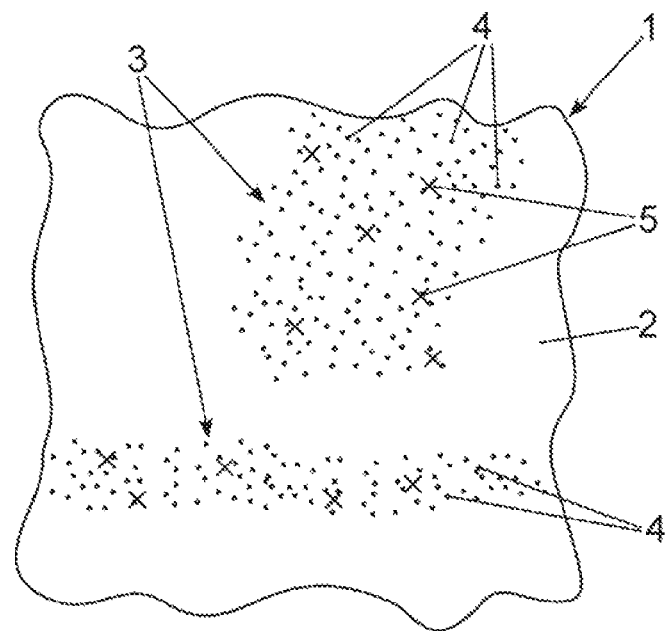
FIG. 1 shows an area of interest of a sample comprising a plurality of molecules of a substance, by which a structure of interest in the sample is marked, only individual molecules of the substance being in a fluorescent state.

Generally, the invention belongs to the field of fluorescence light microscopy. This means that the location of a molecule of the substance in the sample is determined using its fluorescent properties.

When a fluorescent state of a molecule is mentioned here, this means that the molecule, by means of excitation light, can be excited for the emission of fluorescence light but not that the molecule is already in an excited fluorescing state.

Correspondingly, when a non-fluorescent state of a molecule is mentioned here, this means that the molecule, by means of excitation light, cannot be excited for the emission of fluorescence light and that it does also not fluoresce, i.e. that it also does not emit fluorescence light for any other reason. Here, it is only important that the molecule in the non-fluorescent state does not emit the same fluorescence light which is emitted by the molecule, when it is excited in its fluorescent state. Thus, the molecule, in the non-fluorescent state, may for example be excitable for the emission of fluorescence light of another color, i.e. wavelength, which may be distinguished from the fluorescence light emitted by the molecule in its fluorescent state. Particularly, the molecule, in the fluorescent state, may be excitable for the emission of green fluorescence light, and, in the non-fluorescent state, it may be excitable for the emission of red fluorescence light. A non-fluorescent state of the molecule, in which the molecule is by no means excitable for the emission of fluorescence light, is also designated as a dark state here.

The invention provides a method for determining the locations of individual molecules of a substance in a sample, the individual molecules of the substance being in a fluorescent state in which they are, by means of excitation light, excitable for the emission of fluorescence light, distances between the individual molecules of the substance in the fluorescent state keeping a minimum value in an area of interest of the sample.

The method comprises the steps of exciting the individual molecules of the substance for emission of fluorescence light by means of the excitation light, wherein the intensity distribution of the excitation light has at least one local minimum, and of registering the fluorescence light from the excited individual molecules of the substance for different positions of the at least one minimum in the area of interest of the sample.

According to the invention, the minimum value of the distances of the individual molecules of the substance in the area of interest of the sample is $d=\lambda/(2n \sin \alpha \sqrt{(1+I/I_s)})$, wherein $\lambda$ is the wavelength of the excitation light, n is the refraction index of the optical material in which the at least one minimum is formed, $\alpha$ is half the aperture angle of an optical arrangement by which the excitation light is projected into the sample, I is the maximum intensity of the excitation light within the sample, and $I_s$ is a fluorescence excitation saturation intensity of the excitation light depending on the substance. At the fluorescence excitation saturation intensity $I_s$, a certain percentage of the theoretically possible maximum intensity of the fluorescence light is obtained from the molecules of the substance, from which on one may speak of a saturation of the intensity of the fluorescence light. Typically, this percentage is 50% of the theoretically maximum possible intensity of the fluorescence light. The minimum value d corresponds to the spatial resolution which is achieved in the high spatial resolution STED, GSD and RESOLFT scanning fluorescence light microscopy.

It is not necessarily of importance how it is achieved that the distances between the individual molecules of the substance which are in the fluorescent state keep the minimum value d within the area of interest of the sample. It is also not necessary that the distances of all molecules of the substance in the fluorescent state keep the minimum value d. The locations of the fluorescent molecules at a smaller distance may, however, not be determined by means of the method described here.

According to the invention, the intensity of the fluorescence light obtained from a single or individual molecule located in the local minimum of the intensity distribution of the excitation light is at maximum half as high as in an area of the maximum intensity of the excitation light in the sample. It is to be understood that a higher intensity contrast, i.e. a more distinct local minimum in which the intensity of the fluorescence light from an individual molecule drops to a smaller proportion of the maximum intensity of the fluorescence light from the individual molecule, is an advantage. Thus, the intensity of the fluorescence light from the individual molecule may, for example, drop by at least 80% to 20% or less of the maximum intensity, or by at least 90% to 10% or less of the maximum intensity. Ideally, the intensity of the fluorescence light from the individual molecule in the local minimum goes down to zero, i.e. the local minimum ideally is a zero point of the intensity distribution of the excitation light.

According to the invention, the distances between the nearest neighboring positions of the at least one minimum at which the fluorescence light from the excited individual molecules of the sample is registered are not higher than half the minimum value d. According to the invention, the locations of the individual molecules of the substance are then deduced from the course of the intensity of the fluorescence light emitted by the respective molecule over the positions of the at least one minimum in the area of interest of the sample.

If a fluorescent molecule gets into the area of the minimum, the excitation of the molecule for the emission of fluorescence light and thus the intensity of the fluorescence light emitted by it and registered goes down. In the method according to the invention, individual fluorescent molecules are observed. The fluorescence light emitted by these individual fluorescent molecules is separately registered and evaluated. From the course of the intensity of the registered fluorescence light over the positions of the minimum of the excitation light, the location of the respective fluorescent molecule within the sample can thus be determined at an increased spatial resolution or accuracy.

This also applies if the above defined minimum distance $d=\lambda/(2n \sin \alpha \sqrt{(1+I/I_s)})$ of the individual molecules in the sample is clearly smaller than the diffraction limit $\lambda/2n \sin \alpha$ at the wavelength $\lambda$ of the excitation light and also at the wavelength of the fluorescence light, as the maximum intensity I of the excitation light in the sample is typically much higher than the fluorescence excitation saturation intensity $I_s$. Even in this case, the fluorescence light which is registered from the sample may at least be assigned to a small group of individual molecules, and the intensity of the fluorescence light drops by a significant amount every time when one of the molecules gets into the area of the local minimum of the intensity of the excitation light. This drop in intensity of the fluorescence light can be assigned to exactly one individual molecule as long as the minimum distance d of the individual molecules within the sample is kept.

The small distances of the positions of the minimum for which the fluorescence light is registered, i.e. the distance of not more than d/2, ensure that the drop in fluorescence light intensity is actually registered and that its course is spatially resolved. I.e., in the method according to the invention, the area of interest of the sample is scanned with the local minimum of the intensity distribution of the excitation light at increments of d/2 at maximum.

The optical arrangement by which the excitation light is projected into the sample may be an objective lens. It may, however, also be any other optical arrangement by which two partial beams of the excitation light may be superimposed at an angle to form the at least one minimum by means of interference. Then, $\alpha$ is half the angle between these partial beams or the angle between each of the partial beams and the optical axis. n may be the refraction index of the sample, when the minimum is directly formed within the sample, or the refraction index of a material directly neighboring the sample, if the minimum is formed in this material. This is, for example, the case if a similar optical arrangement as in TIRFM (Total Internal Reflection Fluorescence Microscopy) is used for forming the minimum.

As the determination of the locations of the individual molecules is solely based on the intensity of the fluorescence light from the respective molecule determined for each position of the minimum, without considering the exact direction in which the fluorescence light is emitted by the molecule, the method according to the inventions belongs to scanning fluorescence light microscopy; and the determination of the locations of the individual molecules is independent on the orientation of the individual molecules.

For deducing the locations of the individual molecules of the substance from the course of the intensity of the fluorescence light, a function having a local minimum may be fitted to the course of the intensity of the fluorescence light from the respective molecule over the positions of the at least one minimum. Then, the location of the respective molecule may be equated with the position of the local minimum of the fitted function. The function may be a square function. A base form of the fitted function may, however, be individually adapted to the intensity course of the fluorescence light obtained from one molecule of the respective substance in response to the intensity course of the excitation light in the surroundings of the at least one minimum.

It also falls within the scope of the present invention to equate the location of the respective molecule with a position of the at least one minimum in which less fluorescence light is registered from the respective molecule than in any of the nearest neighboring positions of the minimum in any directions. If the minimum or a low excitation area around the minimum, in which the respective molecule is only excited for emission of fluorescence light at a minimum intensity, hits the respective molecule, only this minimum intensity of the fluorescence light from the molecule is registered for this position of the minimum. As this minimum intensity of the fluorescence light may, however, also have other reasons, a position of the minimum in which only the minimum intensity of the fluorescence light from the respective molecule is registered, may only then be equated with the location of the minimum, if for all nearest neighboring positions of the minimum in all different directions more fluorescence light than the minimum intensity is registered. As long as this requirement is fulfilled, this embodiment of the method of the present invention allows for determining the location of the respective molecule in the sample at a spatial accuracy of the dimensions of the low excitation area around the minimum.

When the minimum intensity is zero or close to zero, only very few photons of the fluorescence light are needed from the respective molecule for this kind of determining its location, i.e. only very few photons in the position of the minimum in which the minimum intensity of the fluorescence light is registered and only very few photons more in each of the nearest neighboring position of the minimum in different directions until it is clear that the intensity of the fluorescence light goes beyond the minimum intensity there. Thus, the minimum may very quickly be shifted between its individual positions. With a minimum intensity of zero, it is sufficient to determine whether fluorescence light comes from the respective molecule or not. For this purpose it is sufficient to wait in the respective position for so long as it should take at maximum that at least several photons of the fluorescence light are obtained from the respective molecule. A minimum intensity of zero will, as a rule, only then be realized in a local minimum, if the local minimum is a zero point of the intensity distribution of the excitation light.

If the low excitation area around the minimum shall be used for the determination of the locations of the individual molecules, it has to be ensured that each individual molecule is hit with the low excitation area. This is achieved in that the distances between nearest neighboring positions of the at least one minimum, in which the fluorescence light from the excited individual molecules of the substance is registered, i.e. the increments at which the area of interest of the sample is scanned, are not greater than a diameter of the low excitation area so that the area of interest of the sample is completely scanned with the low excitation area.

If the intensity of the excitation light, adjacent to the at least one minimum, is adjusted so high that a saturation in the intensity of the fluorescence light is achieved, which is emitted by the individual molecules excited by the excitation light, the area of low excitation around the minimum, in which the respective molecule is only excited for emission of fluorescence light at the minimum intensity, and even a surrounding area in which the intensity of the fluorescence light from the respective molecule depends on its distance to the minimum, is strongly spatially delimited. This corresponds to an increase in spatial accuracy of the method according to the invention. This increased spatial accuracy may, however, only be used if the positions of the minimum in the sample in which the intensity of the fluorescence light from the individual molecules is determined are arranged at correspondingly small distances. This is ensured by means of the maximum distance between nearest neighboring positions of the at least one minimum in which the fluorescence light from the excited individual molecules of the substance is registered of d/2.

The individual molecules in the fluorescent state, whose average distance in the area of interest of the sample is higher than the diffraction limit at the wavelength of the excitation light and the fluorescence light, may particularly be realized in that the molecules of the substance, by means of an adjusting signal, are transferable out of their fluorescent state into a non-fluorescent state, or out of a non-fluorescent state into their fluorescent state, a transition probability between these states increasing with the intensity of the adjusting signal (until a saturation is reached). Then, with such a high density of the molecules in the area of interest of the sample that the distances between nearest neighboring molecules of the substance are smaller than the minimum value d, in each instant, only a proportion of the molecules will be left in the fluorescent state or transferred into the fluorescent state by the adjusting signal. This proportion of the molecules of the substance, by means of the intensity of the adjusting signal, can be adjusted such that the distances between the individual molecules of the substance in the fluorescent state keep the minimum value d. As it depends on transition probabilities which molecules of the substance belong to this proportion which is in the fluorescent state in each instant, the locations of different molecules of the substance in the sample may successively be determined.

The ways in which one deals with molecules whose locations have already been determined may be different. Generally, they may be bleached permanently. In another embodiment, they may, under the influence of a return signal or spontaneously, i.e. only by means of thermal excitation, return into their original non-fluorescent state. Further, they may, by means of the adjustment signal, be transferred into their non-fluorescent state like most of the other molecules. Then, by means of repeatedly or continuously applying the adjusting signal and, if used, the return signal, the distances between nearest neighbors may be adjusted to the minimum value d for always other individual molecules in the fluorescent state. If the locations of all these individual molecules in the fluorescent state are determined, an image of the distribution of the molecules of the substance in the sample is successively obtained.

During successively determining the locations of different proportions of the substance, the sample may continuously or intermittently be subjected to the adjusting signal and, if used, to the return signal. Registering the fluorescence light from the sample may also occur continuously or intermittently. In any case, registering the fluorescence light is separately carried out for each position of the minimum of the excitation light within the sample. This, however, does not exclude that the position of the minimum in the sample is continuously moved, as long as the minimum, during each period of time for which the fluorescence light is registered, does only move little, and never more than d/4.

The adjusting signal, by which the molecules of the substance are transferred between their fluorescent state and their non-fluorescent state to adjust a proportion of the molecules in the fluorescent state in which the distances between nearest neighbors keep the minimum value, may generally be any chemical or physical signal. Preferably, the adjusting signal is adjusting light.

By means of the adjusting light, the molecules of the substance may be transferred out of their fluorescent state into their non-fluorescent state, only the non-fluorescent state of the molecules of the substance being an electronic energy state. In the latter case, the adjusting light typically excites the fluorescent molecules of the substance also for emission of fluorescence light, and they will be transferred into the non-fluorescent state only after the emission of some photons of the fluorescence light. Thus, in the method according to the invention, the adjusting light may also be the excitation light so that only light of one wavelength has to be used.

When comparing the embodiment of the method according to the invention described at last with the method known as GSDIM, the invention, similar as GSDIM, is a method of determining the locations of individual molecules of a substance in a sample to obtain a spatially high resolution image of a distribution of the molecules of the substance in the sample, wherein the molecules, at the beginning or start, are in a fluorescent state, wherein the molecules of the substance in their fluorescent state, by means of excitation light, are excitable for emission of fluorescence light, wherein the molecules of the substance, by means of the excitation light, are transferable out of their fluorescent state into an non-fluorescent dark state, wherein the molecules of the substance return out of their non-fluorescent state into their fluorescent state, and wherein the distances between the molecules of the substance in the sample are, per se, smaller than a minimum value.

Still similar as GSDIM, this embodiment of the method according to the invention comprises the steps of, by means of the excitation light, adjusting such a proportion of the molecules of the substance in the fluorescent state that distances between the molecules of the substance which are at present in the fluorescent state keep the minimum value within an area of interest of the sample, and of registering the fluorescence light from the molecules of the substance in the fluorescent state, which have been excited by the excitation light.

Additionally, according to the invention, the minimum value of the distances of the individual molecules of the substance in the area of interest of the sample is $d=\lambda/(2n \sin \alpha \sqrt{(1+I/I_s)})$. The intensity distribution of the excitation light comprises at least one local minimum, wherein the intensity of the fluorescence light from an individual molecule at the location of the local minimum of the intensity distribution is at maximum half as high as at a location of maximum intensity of the excitation light within the sample. The position of the at least one local minimum in the area of interest of the sample is varied. The fluorescence light from the molecules of the substance in the fluorescent state excited by means of the excitation light is registered for different positions of the at least one local minimum within the sample for a registering area including the at least one local minimum separately with regard to fluorescence light emitted out of other areas of the sample. Here, distances between nearest neighboring positions of the at least one local minimum, in which the fluorescence light from the excited individual molecules of the sample is registered, are not more than half the minimum value d. I.e., the area of interest of the sample is scanned in increments with the at least one local minimum which are not greater than d/2.

The locations of the individual molecules of the substance are then deduced from the course of the intensity of the fluorescence light emitted out of the registering area over the positions of the at least one local minimum in the area of interest of the sample. This deduction of the locations of the individual molecules from the course of the intensity of the fluorescence light may take place in exactly the same way as already explained in the above examples. The adjustment of the intensity of the excitation light and the distances between nearest neighboring positions of the at least one local minimum may also take place in the same way as described above.

The at least one local minimum may particularly be a point-shaped minimum, whose position within the area of interest of the sample is varied in all dimensions of the sample, i.e. in two directions with a two-dimensional sample, and in three directions with a three-dimensional sample. With a point-shaped minimum, the locations of the individual molecules of the substance in all dimensions of the sample may be deduced from the course of the intensity of the fluorescence light from the respective molecule over the positions of the at least one local minimum in the area of interest of the sample. It is to be understood that, suitably, the course of the intensity of the fluorescence light over the positions of the minimum is considered in all dimensions of the sample. Correspondingly, in case of the two- or three-dimensional sample, a two- or three-dimensional function with a minimum is to be fitted to the course of the intensity of the fluorescence light.

With a point-shaped minimum, the fluorescence light out of one registering area including the at least one minimum can be registered by means of a point detector confocally arranged with regard to the respective minimum. The registering area may then have dimensions of at least several, preferably at least three distances of the positions of the minimum and be concentrically arranged with regard to the minimum.

The at least one minimum may also extend along a line or plane. Then, the position of the minimum in the area of interest of the sample is varied in a scanning direction orthogonal to this line or plane. The locations of the individual molecules of the substance in the scanning direction are then determined from the course of the intensity of the fluorescence light from the respective molecule over the positions of the at least one local minimum. The line or plane may be oriented differently with regard to the sample and be shifted in correspondingly different scanning directions with regard to the sample to determine the locations of the individual molecules in further directions. The locations of the individual molecules in the further directions may, however, also be determined in another way, like for example by means of localization.

The intensity distribution of the excitation light may not only have one minimum but a plurality of local minima. The positions of these several minima in the area of interest of the sample are then varied simultaneously, the fluorescence light from the excited individual molecules of the substance being separately registered for each minimum. Particularly, the minima can be arranged as a grating. With point-shaped minima, the grating may be one- or two-dimensional. The distances between the several minima must, in any case, be higher than the diffraction limit at the wavelength of the fluorescence light. The distances between the several minima have also to be greater than any registering areas out of which the fluorescence light for each minimum is registered. Preferably, the distances between the minima are several times greater than the distances between the positions in which the individual minima are arranged within the sample to measure the associated intensities of the fluorescence light. Preferably, the distances of the minima are at least thrice as high as the distances of the positions of the minima within the sample in which the fluorescence light is measured.

The fluorescence light from the individual fluorescent molecules in the sample may be registered with a light sensor array which is fixed with regard to the sample and onto which the sample is imaged, e.g. by means of a digital camera, like for example a CCD or CMOS camera. When the distances of the individual molecules of the substance in the area of interest of the sample are also greater than the diffraction limit at the wavelength of the fluorescence light, the locations of the individual molecules of the substance may additionally be determined by means of localization from the distribution of the total fluorescence light over the light sensor array, wherein the total fluorescence light includes all the fluorescence light emitted by the sample, i.e. independently on the position of the minimum of the intensity distribution of the excitation light. Thus, the same photons of the fluorescence light by which the locations of the molecules have been determined depending on the positions of the minimum within the sample are also used for a second determination of their locations using their distribution over the light sensor array, wherein the minimum and its movement with regard to the sample is irrelevant. The results of these two methods in determining the locations of the molecules may be combined to increasing the oval accuracy in determining the locations of the individual molecules.

If some of distances of the individual molecules of the substance in the area of interest of the sample are smaller than the diffraction limit at the wavelength of the fluorescence light so that the fluorescence light may not be separately assigned to the respective molecules, the locations of the molecules may be determined using more complex localization algorithms. In these algorithms, the locations determined according to the method of the invention may be entered as starting values.

If different locations are determined for the individual molecules according to the method of the invention and by means of localization, the differences between the locations may be evaluated with regard to a fixed orientation of the individual molecules within the sample. This option is based on the fact that the determination of the locations of the molecules of the substance within the sample depending on the distribution of the registered fluorescence light over the light sensor array depends on a fixed orientation of the molecules, which this dependency is not present in determining the locations by means of the shifted minimum.

Thus, the method according to the invention can be carried out as a supplement to any of the known methods like PALM, STORM, GSDIM and the like without disturbing the known method but providing additional localization information with regard to the individual molecules in another way, even if the same registered photons are evaluated.

If the fluorescence light is registered by means of a light sensor array, frames may be continuously read out of the light sensor array and assigned to the respective positions of the at least one minimum in the sample. Here, several frames may be assigned to one position, but it is not allowed to assign several positions of the minimum to one frame. This, however, does not exclude that the at least one minimum is continuously shifted within the sample, if the motion blur introduced in this way remains small.

An apparatus according to the invention which is suited for carrying out preferred embodiments of the method according to the invention comprises an excitation light source providing excitation light by which molecules of a substance which are in a fluorescent state are excitable for the emission of fluorescence light and by which the molecules of the substance out of their fluorescent state are transferable into a non-fluorescent state. Additionally, there is an optical arrangement which projects the excitation light into the sample. A detector device registers the fluorescence light which is emitted by the molecules of the substance in the fluorescent state excited by means of the excitation light. According to the invention, a light shaping optic forms an intensity distribution of the excitation light in the sample which has at least one local minimum, wherein the intensity of the fluorescence light from a single molecule at the location of the local minimum of the intensity distribution of the excitation light is at maximum half as high as at a location of maximum intensity of the excitation light in the sample. Further, a scanning device is provided by which the at least one minimum of the excitation light can be positioned into different positions within the sample. The detector device registers the fluorescence light emitted out of a diffraction-delimited registering area including the at least one minimum separately from fluorescence light emitted out of other areas of the sample. Distances between nearest neighboring positions of the at least one minimum in which the detector device registers the fluorescence light out of the registering area are not greater than $\lambda/(4n \sin \alpha \sqrt{(1+I/I_s)})$, i.e. the scanning device scans an area of interest of the sample in increments which are not higher than half the minimum value d.

Preferably, the light shaping optic forms the excitation light as a grating of local minima which is projected into the sample. The scanning device shifts the intensity distribution with regard to the sample in such a way that an area of interest of the sample is completely scanned with the low excitation areas around the minima within which the substance is essentially not excited for the emission of fluorescence. How a grating of zero points can be realized is described in Chmyrov, A. et al: Nanoscopy with more than 100,000 'doughnuts', Nature Methods 10 737-740 (2013).

For delimiting the at least one local minimum or the local minima in a three-dimensional sample in z-direction of the optical axis, one may make use of the 4Pi method. Here, the same measures for forming a minimum in z-direction may be taken as described in Schmidt, R. et al.: Spherical nanosized focal spot unravels the interior of cells, Nature Meth, 5, 539-544 (2008) with respect to forming the intensity distribution of the STED beam in the same direction. When coherent partial beams of the excitation light are directed in the sample through two oppositely oriented or facing objective lenses and brought to interference within the sample, even three-dimensional gratings of local minima can be formed within the sample.

The detector device preferably comprises an image sensor array which is fixed with regard to the sample, even during operation of the scanning device, and onto which the sample is imaged. This image sensor array may be realized as a CCD or CMOS camera.

Referring now in greater detail to the drawings, FIG. 1 shows an area 1 of interest of a sample 2 in which a structure 3 is marked with molecules 4 of a substance having a fluorescent state and a non-fluorescent state. With regard to all molecules 4, i.e. independently on their state, the molecules 4 are present at vary small distances to their nearest neighbors. These distances are smaller than the diffraction limit at the wavelength of fluorescence light which can be obtained from the molecules 4 when they are, in their fluorescent state, excited by means of excitation light. The distances are also smaller than a minimum value $d=\lambda/(2n \sin \alpha \sqrt{(1+I/I_s)})$, wherein $\lambda$ is the wavelength of the excitation light, n is the refraction index of the optical material in which the at least one minimum if formed, $\alpha$ is half the aperture angle of an optical arrangement by which the excitation light is projected into the sample, I is the maximum intensity of the excitation light within the sample 2, and $I_s$ is a fluorescence excitation saturation intensity of the excitation light depending on the actual substance. This minimum value d corresponds to the accuracy in spatial imaging which is achieved in spatial high resolution STED, GSD and RESOLFT scanning fluorescence light microscopy.

However, only single or individual molecules 5 which are each marked with an "x" in FIG. 1 are in the fluorescent state, whereas the other molecules which are only depicted by dots in FIG. 1 are in the non-fluorescent state and are thus not excited for the emission of fluorescence light by means of the excitation light. The individual fluorescent molecules 5, i.e. the molecules 5 in the fluorescent state, are arranged at distances within the area 1 of interest which keep the minimum value d, i.e. which are at least as high as the minimum value d, and which preferably also keeps the diffraction limit at the wavelength of the fluorescence light. The latter fact allows for separately registering the fluorescence light emitted by the individual molecules 5, i.e. for separately registering and separately assigning the fluorescence light to a certain individual molecule 5. Adjusting a correspondingly small proportion of the molecules 4 within the fluorescent state 5 may be achieved in different ways as they are generally known from the methods known as PALM, STORM and GSDIM.

Figure 2:
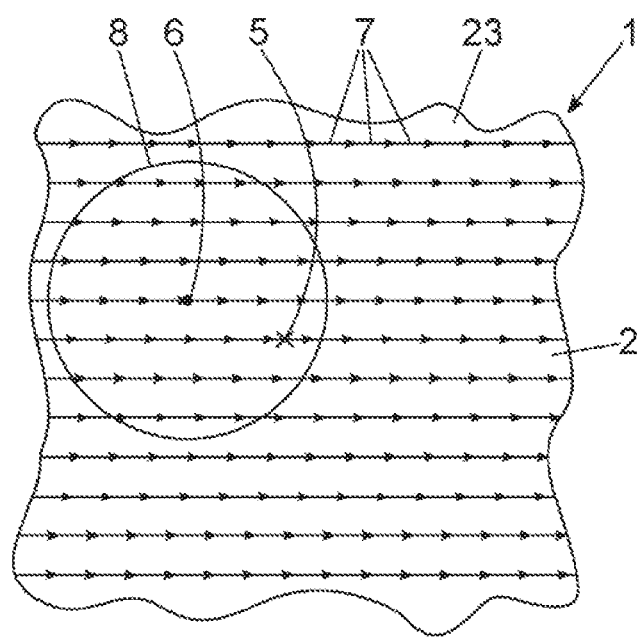
FIG. 2, for an area of interest of the sample, shows scanning with a local minimum of an intensity distribution of excitation light, only one individual molecule in the fluorescent sample being depicted.

FIG. 2 illustrates how the respective area 1 of interest of the sample 2 is subjected to the excitation light 23 and scanned with a local minimum 6 of an intensity distribution of the excitation light 23 in increments indicated by arrows. These increments and the resulting distances 7 of nearest neighboring positions of the minimum 6 within the sample 2 are not greater than half the diffraction limit at the wavelength of the excitation light and the fluorescence light emitted by the individual molecules 5 due to the excitation by means of the excitation light. In FIG. 2 only a single molecule in the fluorescent state is indicated by means of an "x". In an area 8 around the minimum 6, the intensity of the fluorescence light emitted by the respective individual molecule 5 depends on its distance to the minimum 6. Outside the area 8, this intensity of the fluorescence light shall be saturated here. This means that the intensity of the excitation light 23 outside the area 8 is so high that a maximum intensity of the fluorescence light is obtained from the individual molecules 5 independent on their actual location.

Figure 3:
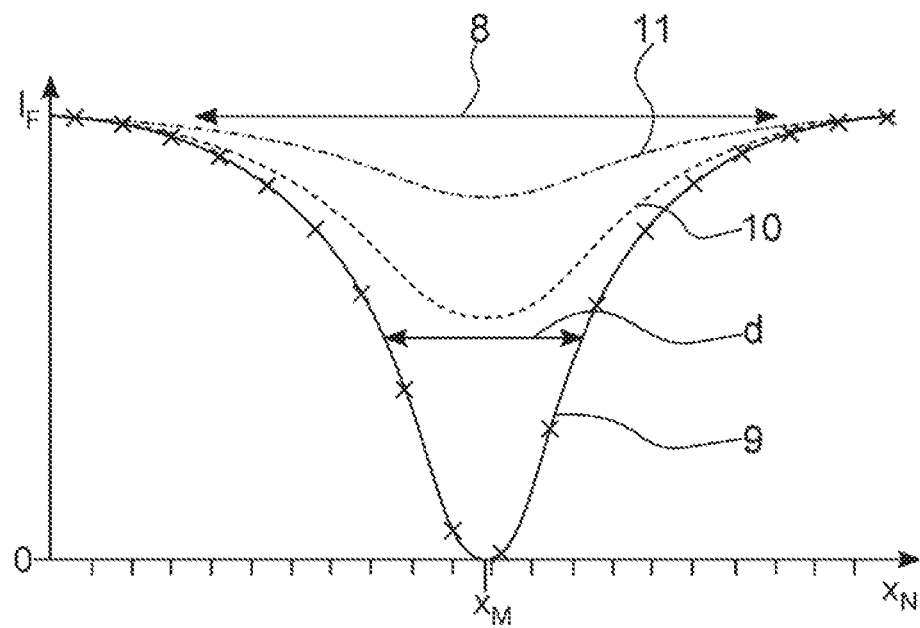
FIG. 3 is a plot of the intensity of the fluorescence light registered from the individual fluorescent molecule according to FIG. 2 over the different positions of the minimum.

FIG. 3 shows the intensity $I_F$ of the fluorescence light obtained from an individual molecule 5 which is passed over by the point-shaped minimum 6 according to FIG. 2, the molecule 5 according to FIG. 2 being exactly passed over but not exactly hit with one of the positions $x_N$ of the minimum 6 in which the intensity $I_F$ of the fluorescence light is measured. In FIG. 3 the registered intensities $I_F$ of the fluorescence light are indicated, each by means of an "x", over the various positions $x_N$ of the minimum 6 within the sample 2. Here, the minimum 6 is a zero point of the intensity of the excitation light 23, and thus the intensity $I_F$ of the fluorescence light also displays a zero point. At least, the intensity $I_F$ of the fluorescence light from a molecule 5 within the minimum decreases to 50% of the intensity $I_F$ of the fluorescence light outside the area 8. If a function 9 having a local minimum is fitted to the course of the intensities $I_F$ registered for the positions $x_N$, the location $x_M$ of the molecule within the sample may be deduced from the position of the minimum at a higher spatial accuracy than the distance of the positions $x_N$. The distance of the positions $x_N$ is not higher than half the minimum value d. Here, it is even smaller than the minimum value d. The minimum value d corresponds to the full width at half maximum of the course of the intensity $I_F$ influenced or deformed by the minimum 6.

The function 9 having the local minimum may be adapted to the expected course of the intensity $I_F$ when passing over the molecule 5 with the minimum 6 according to FIG. 2. With a dashed line 10, a corresponding course of the intensity $I_F$ of the fluorescence light, when the minimum 6 according to FIG. 2 misses the molecule 5 by one line, is depicted in FIG. 3. A dashed-dotted line 11 indicates the course of the intensity $I_F$ when missing the molecule by two lines. Thus, the location of the molecule may also be determined in the y-direction orthogonal to the x-direction from the corresponding real measurement values of the intensity $I_F$ of the fluorescence light.

Figure 4:
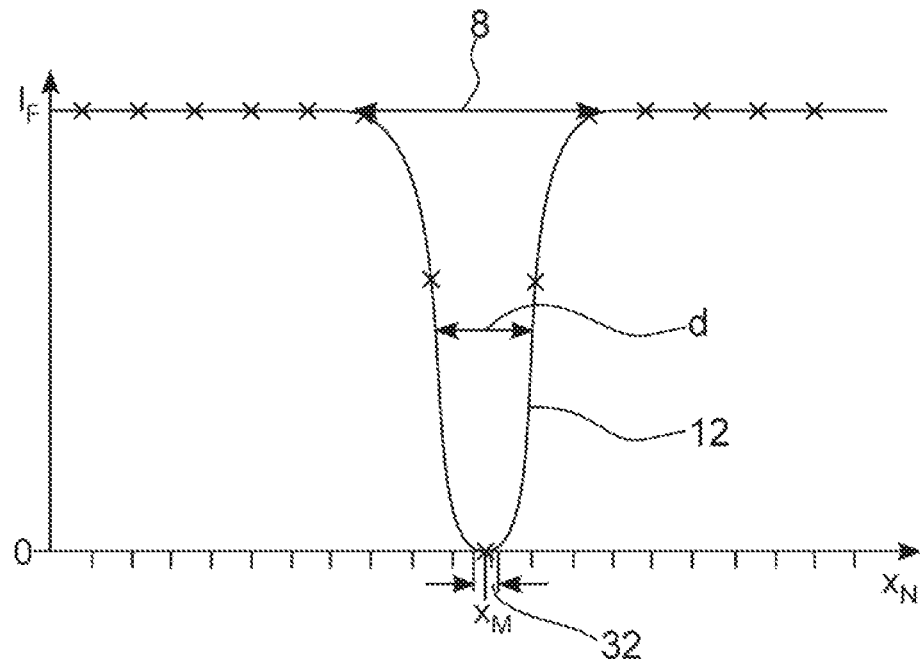
FIG. 4 is a plot of the intensity of the fluorescence light registered from the individual fluorescent molecule according to FIG. 2, when scanning the sample with the minimum at a considerably higher maximum intensity of the excitation light.

FIG. 4 indicates the course 12 of the intensity $I_F$ of the fluorescence light over the different positions $x_N$ of the minimum 6 according to FIG. 2 in form of a zero point for a much higher absolute intensity of the excitation light 23 outside the minimum 6. Here, outside a low excitation area 32 directly around the minimum 6, a saturation of the intensity $I_F$ of the fluorescence light which is emitted by the respective fluorescent molecule 5 is quickly reached. Under these boundary conditions, the position $x_N$ of the minimum 6 at which the intensity $I_F$ of the fluorescence light of zero is registered can be equated with the location of the molecule $x_M$, if any fluorescence light from the respective fluorescent molecule 5 is registered in any other position $x_N$ of the minimum 6 adjacent to this distinguished position $x_N$.

Figure 5:
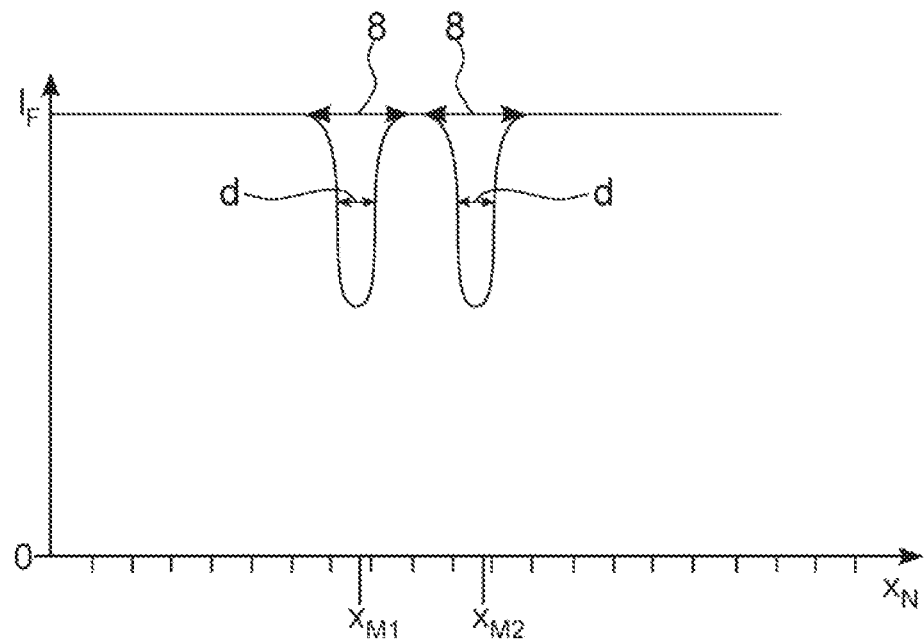
FIG. 5 is a plot of the intensity of the fluorescence light emitted by two individual fluorescent molecules, when scanning the sample with the minimum at the high maximum intensity of the excitation light according to FIG. 4.

FIG. 5 shows the course of the intensity $I_F$ of the fluorescence light over the positions $x_N$ of the minimum in the sample in case of two molecules 5 in the fluorescent state which are arranged at a very small distance within the sample 2. This small distance is much smaller than the diffraction limit at the wavelength of the fluorescence light. Thus, the intensity $I_F$ cannot be separately assigned to the individual molecules 5 by means of a light sensor array onto which the sample 2 is imaged. The decrease in intensity $I_F$ of the fluorescence light over the position $x_N$ of the minimum, however, separately occurs for the two molecules, if the intensity of the excitation light 23 is adapted to the minimum distance of the molecules. This is due to the fact that both the dimensions of the area 8 and the minimum value d which corresponds to the full width at half maximum of the intensity $I_F$ in the area of the minimum decrease with the increasing intensity of the excitation light. If the distance of the molecules 5 is at least as great as the above defined minimum value d, the intensity $I_F$ of the fluorescence light at a position of the minimum 6 between the molecules 5 increases again so that the individual decreases in intensity $I_F$ can be assigned to the individual molecules.

In FIG. 5 a case is depicted in which even the intensity $I_F$ of the fluorescence light from one individual fluorescent molecule 5 that is fully hit by the minimum 6 goes not down to zero because the minimum 6 is no zero point here. Instead, the intensity $I_F$ only goes down to about 90% of its maximum value when one of the molecules 5 gets into the area of the minimum 6.

As long as the drop in intensity $I_F$ is at least 50%, this does not affect the determination of the locations $x_{M1}$ and $x_{M2}$ of the individual molecules from the course of the intensity $I_F$.

Figure 6:
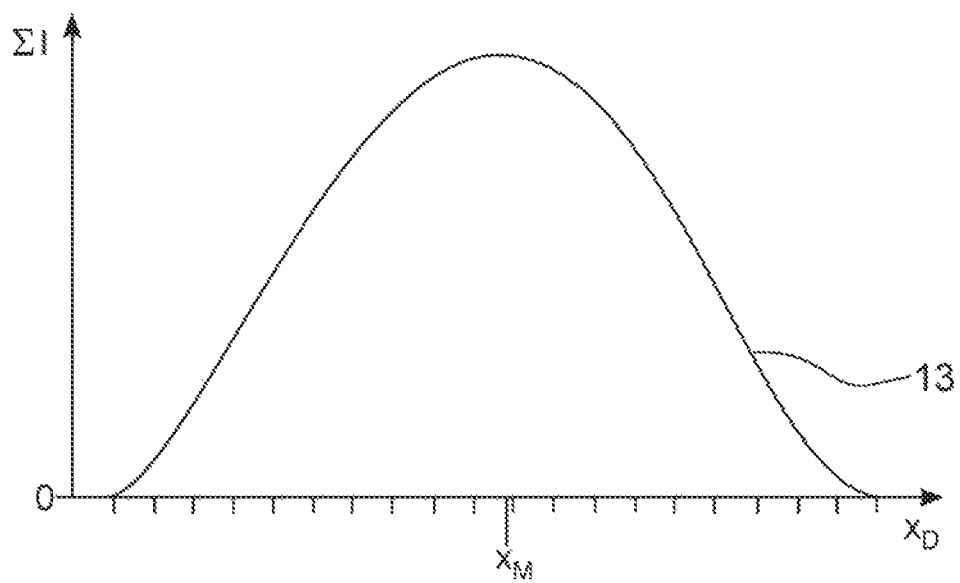
FIG. 6 is a section through the distribution of the total fluorescence light emitted by one individual fluorescent molecule over the light sensor array used for registering the fluorescent light.

FIG. 6 shows the intensity $\Sigma I$ of the fluorescence light from an individual molecule 5 summed up over the individual positions $x_N$ in a section through the distribution of the summed up intensities $\Sigma I$ over a light sensor array onto which the sample is imaged and by which the fluorescence light is registered. Whereas, for the evaluation illustrated in FIGS. 3 and 4 it was only important which intensity I of the fluorescence light from the individual fluorescent molecule 5 is registered for which position $x_N$ of the minimum 6 but not where this fluorescence light is registered, as long as it can be assigned to the individual fluorescent molecule 5, according to FIG. 6, the distribution 13 of the overall fluorescence light registered for the individual fluorescent molecule 5 over the light sensor array is evaluated. From the center of this spatial distribution 13, the location of the molecule within the sample may also be determined, independent on the position of the minimum 6 and in a way which is known as localization. Here, the apparent location $x'_M$ of the molecule 5 within the sample 2 may, however, depend on a fixed orientation and thus on an always identically oriented electric dipole moment of the molecule within the sample 2 resulting in a spatial directional distribution of the emitted fluorescence light (see Engelhardt, J. et al., Molecular orientation affects localization accuracy in superresolution far-field fluorescence microscopy, Nano Lett. 2011, Jan. 12; 11(1):209-13). This is not the case in the method for determining the location of the molecule explained with reference to FIGS. 3 and 4.

Figure 7:
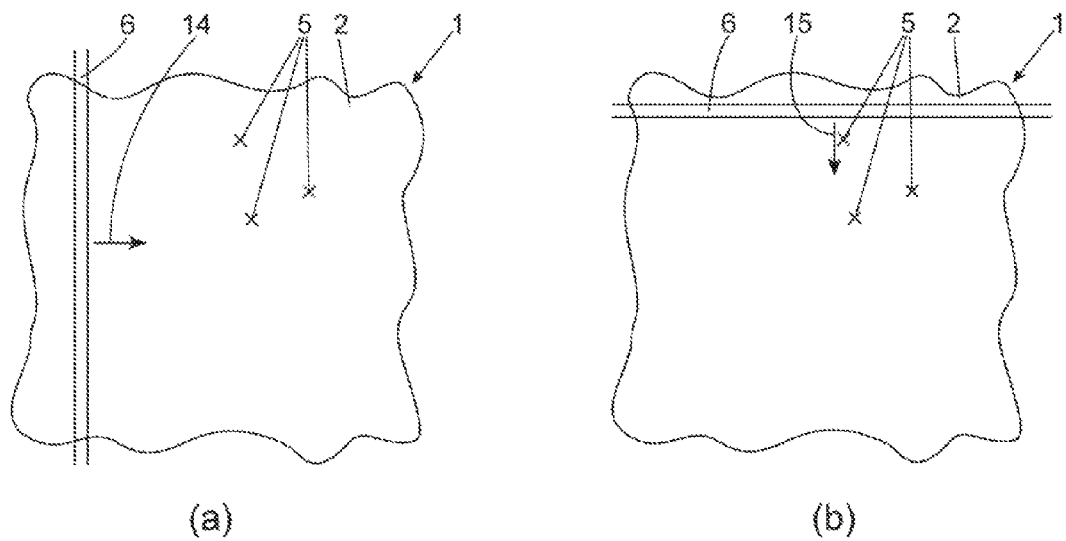
FIG. 7 illustrate scanning of an area of interest of a sample with a line-shaped zero point in two different directions.

FIG. 2 depicts a point-shaped minimum 6. With such a point-shaped minimum 6, the position of each individual fluorescent molecule within a sample can be determined by scanning the sample once—which means scanning a two-dimensional sample in two directions and a three-dimensional sample in three directions. If a line-shaped minimum according to FIG. 7 or a minimum in form of a plane orthogonal to the drawing plane is used, the sample is to be scanned in a direction orthogonal to the direction of main extension of the minimum with the minimum to determine the locations of the fluorescent molecules in the respective scanning direction 14, 15. Correspondingly, a two-dimensional sample has to scanned in at least two, preferably orthogonal, scanning directions 14, 15 as depicted in FIGS. 7(a) and(b) to completely determine the locations of the individual molecules. Here, several fluorescent molecules 5 may simultaneously be in the area of a minimum in form of a line of plane as long as the fluorescence light emitted by each of the molecules can be registered separately or separated.

There is no need that the excitation light 23 is applied to the entire sample or the entire area 1 of interest of the sample 2 outside the minimum 6 with such an intensity that fluorescence light from the individual molecules 5 may always be registered as long as they are not exactly with the low excitation area 32 around the minimum 6. Instead, the intensity of the excitation light 23 may be focused or concentrated to an area around the minimum 6. Here, this area may end with a further minimum behind which the intensity of the excitation light 23 increases again, or the intensity of the excitation light 23 may decay. Whereas, in the first case, the further minimum may also be used for determining the location of the individual molecules 5, in the second case, the variation in intensity $I_F$ of the fluorescence light from a fluorescent molecule 5 over a higher number of positions $x_N$ of the minimum 6 in the sample 2 will be noticed and may thus be considered in determining the location $x_M$ of the respective fluorescent molecule 5.

Figure 8:
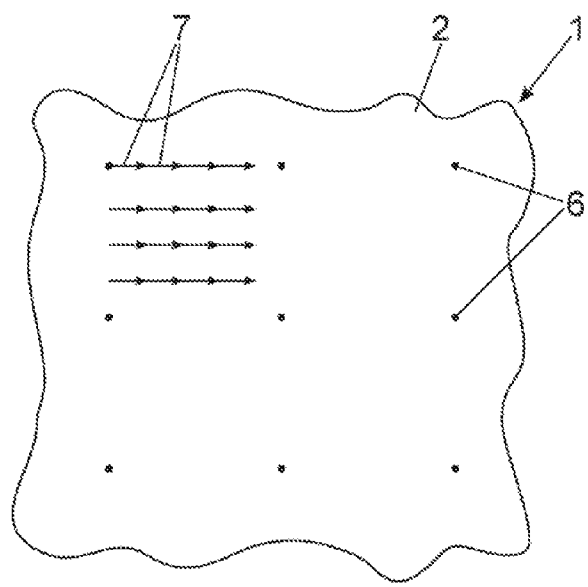
FIG. 8 illustrates scanning of an area of interest of a sample with a grating of dot-shaped zero points.

FIG. 8 illustrates, how the area 1 of interest of the sample 2, with a grating of point-shaped local minima 6, can be scanned in a much smaller number of steps or with much less increments than with only one minimum 6 according to FIG. 2. Here, even for scanning nearly the entire depicted area 1 of interest, only four minima are sufficient, each of which approaching 20 positions within the plane. Such a pattern of minima as depicted in FIG. 4 may generally be realized by superposition of orthogonally oriented line gratings which are generated by superposition of coherent partial beams (see Chmyrov, A. et al: Nanoscopy with more than 100,000 'doughnuts', Nature methods 10 737-740 (2013)).

Figure 9:
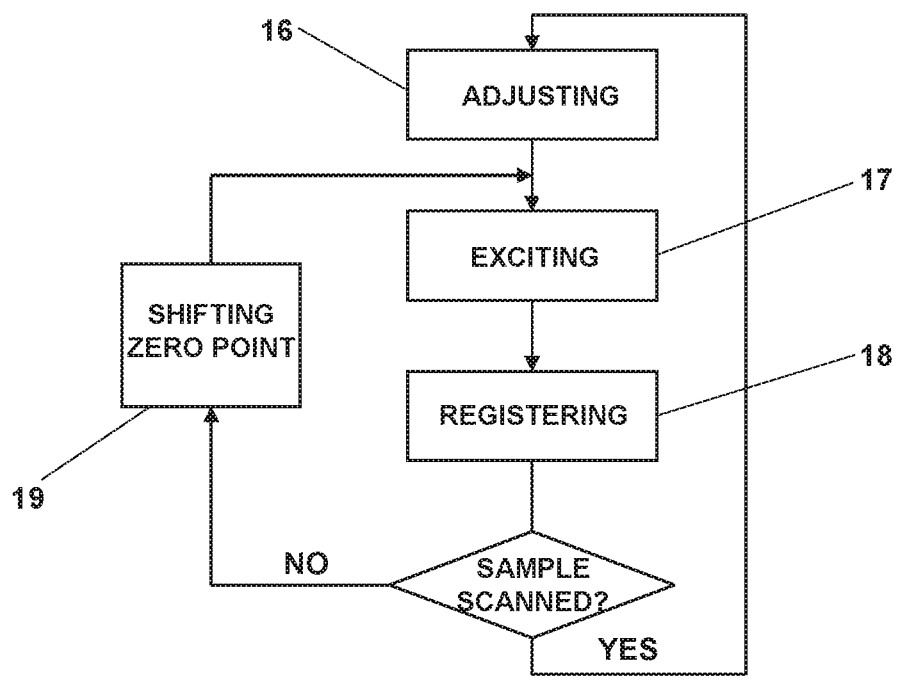
FIG. 9 is a flowchart of an embodiment of the method according to the invention.

FIG. 9 illustrates the general sequence of steps of a method according to the invention. In a step 16, the proportion of the total number of molecules 4 of the substance is adjusted which make the individual molecules 5 in the fluorescent state. In a step 17, the molecules 5 in the fluorescent state are excited for emission of fluorescence light by means of the intensity distribution of the excitation light 23 which has the at least one local minimum 6. In a step 18, this fluorescence light is registered and assigned to the actual position of the minimum 6 within the sample 2. Then, in a step 19, the minimum 6 is shifted over a small distance of not more than d/2 with regard to its previous position. Afterwards, the steps of exciting 17, registering 18 and shifting 19 are repeated until the entire sample is scanned with the minimum 6. Then, a new proportion of the molecules 4 of the substance is transferred into the fluorescent state, i.e. in a repetition of step 16 other individual molecules 5 are randomly selected, followed by a repetition of the loop including the steps 17 to 19. The steps 16 to 19 illustrated in FIG. 9 are carried out as long as the locations of so many individual molecules 5 in the sample 2 have been determined that these locations represent the totality of the molecules 4 within the sample at the desired accuracy. For this purpose, it is not required that the positions of all molecules 4 within the sample 2 are determined. Instead, it is sufficient to determine the locations of a sufficient number of representatives of the molecules 4 in form of the individual fluorescent molecules 5.

If the fluorescence light in step 18 of the method illustrated in FIG. 9 is registered by means of a light sensor array onto which a sample 2 is imaged, the distribution 13 of the overall fluorescence light of the light sensor array registered for each individual fluorescent molecule 5 may also be used to determine its position by means of localization (see FIG. 6).

Figure 10:
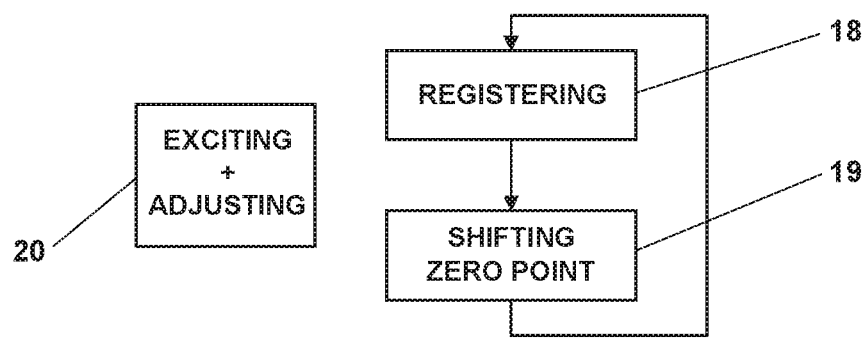
FIG. 10 is a flowchart of another embodiment of the method according to the invention.

In a method according to the invention, the steps 16 to 19 separately depicted in FIG. 9 may also he combined. This is illustrated in FIG. 10. Here, in a step 20, by means of excitation light which also serves as adjusting light, it is ensured that the individual molecules 5 which remain in the fluorescent state have a sufficiently great distance with regard to each other to be able to separately register the fluorescence light emitted by them, and these individual molecules 5, at least outside the at least one minimum 6 of the distribution of the excitation light 23, are excited for the emission of fluorescence light.

In parallel to step 20, a loop of the steps of registering 18 the fluorescence light from the individual fluorescent molecules 5 in the sample 2 and of shifting 19 the minimum 6 runs. Shifting 19 the minimum 6 may even be carried out continuously, if the resulting movement of the minimum 6 within the sample 2 within each period of time for which the intensity $I_F$ of the fluorescence light is registered remains small as compared to the desired accuracy in determining the locations of the molecules 5.

That this method according to the invention can be executed was a surprise even in view of the public knowledge with regard to GSD microscopy with a single wavelength, see U.S. Pat. No. 7,485,875 B2, corresponding to DE 10 2005 034 443 A1 and GSDIM. Namely, the method according to the invention requires that the molecules 4 getting into the area of the minimum 6 of the excitation light 23 do not directly get back into their fluorescent state due to the decrease of the intensity of the excitation light 23, but that the distribution of the individual molecules 5 still in their fluorescent state which has been adjusted by the intensity of the excitation light 23 remains unchanged for a period of time of sufficient length to scan the area 1 of interest of the sample 2 with the minimum 6. At least for local minima 6 with a small area 8 and thus with an even smaller full width of half maximum d and with a quick movement of the minima 6 as compared to the duration for with which each individual molecule 5 is in its fluorescent state, the reduced intensity of the excitation light 23 in the minima 6 has little effect on the division of the molecules 4 of the substance into their fluorescent state and into their non-fluorescent state. Thus, the locations of the individual molecules 5 can be determined during the duration in which they are in their fluorescent state, and this determination is not inhibited by molecules 4 getting back into their fluorescent state in the area of the minima. For the methods according to the invention, it may be required to adjust the transition probabilities between the fluorescent and the non-fluorescent state of the molecules 4, which are particularly defined by the intensity of the excitation light 23, in a suitable way. For this purpose, suitable chemicals may, for example, be added to the sample 2, or the concentration of oxygen within the sample 2 may be suitably adjusted. Minima 6 only having a small low excitation area 32 may also be helpful, which are shifted quickly between their individual positions within the sample 2.

Figure 11:
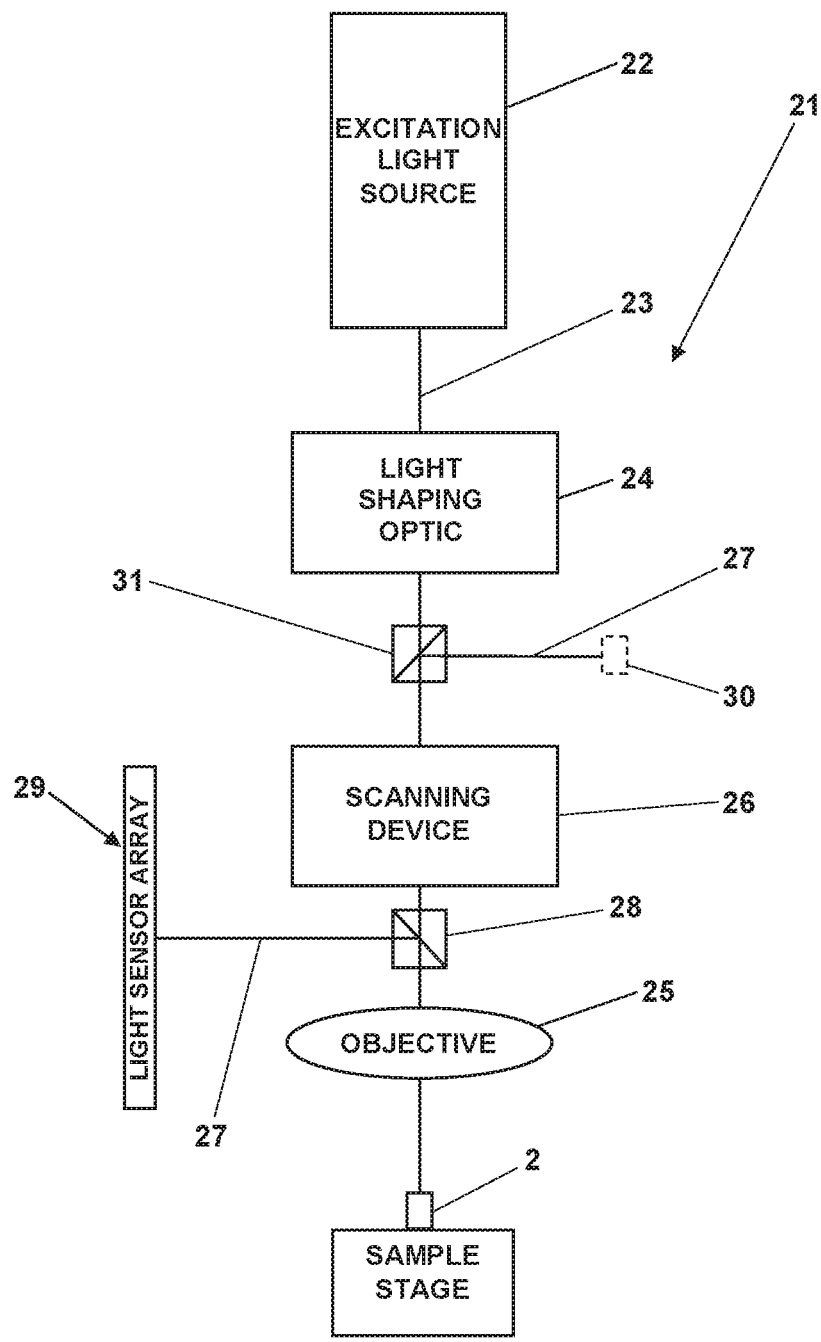
FIG. 11 illustrates the apparatus according to the invention.

FIG. 11 illustrates an apparatus 21 for carrying out the method according to the invention. The apparatus comprises an excitation light source 22 providing the excitation light 23. A light shaping optic 24 shapes the excitation light 23 in such a way that it, after being focused by an objective lens 25, comprises the desired intensity distribution comprising the at least one minimum 6 with the sample 2. For the purpose of shifting the minimum 6 in increments of at least d/2 within the sample 2, a scanning device 26 is provided. The fluorescence light 27 coming from the sample 2 is deflected towards a light sensor array 26 by means of a beam splitter 28. The sample 2 is imaged onto the light sensor array 29 by means of the objective lens 25. The light sensor array 29 allows for evaluating the registered intensity of the fluorescence light 27 emitted out of the sample 2 also for localization of the individual molecules 5 within the sample 2. For the determination of the locations of the individual molecules 5 in the sample 2 according to the present invention, however, a point detector 30 depicted with a dashed line is sufficient. The fluorescence light 27 is deflected towards the point detector 30 by a further beam splitter 31 which, from a point of view of the sample 2, is arranged behind the scanning device 26. The point detector 30 registers the fluorescence light coming out of a registration area including the minimum 6. The scanning device 26 may be designed such that it sets the positions of the minimum 6 of the excitation light 23 for which the fluorescence light 27 from the sample 2 is registered so densely that their distances 7 are not greater than the diffraction limit at the wavelength of the excitation light 23 and the fluorescence light 27. Preferably, these distances are not greater than d/2.

Many variations and modifications may be made to the preferred embodiments of the invention without departing substantially from the spirit and principles of the invention. All such modifications and variations are intended to be included herein within the scope of the present invention, as defined by the following claims.

I claim:

1. A method of determining the locations of individual molecules of a substance in a sample, wherein the individual molecules of the substance are in a fluorescent state in which they are excitable for emission of fluorescence light by means of excitation light, the method comprising:
    forming an intensity distribution of the excitation light comprising at least one local minimum of the intensity of the excitation light;
    exciting the individual molecules of the substance in the fluorescent state for the emission of the fluorescence light by means of the excitation light;
    registering an intensity of the fluorescence light emitted by the excited individual molecules of the substance in the fluorescent state for different positions of the at least one minimum in an area of interest of the sample; and
    deducing the locations of the individual molecules of the substance in the fluorescent state from a course of the registered intensity of the fluorescence light over the positions of the at least one minimum in the area of interest of the sample;
    wherein distances between the individual molecules of the substance in the fluorescent state keep a minimum value $d=\lambda/(2n \sin \alpha\sqrt{(1+I/I_s)})$ in the area of interest of the sample, wherein
        $\lambda$ is a wavelength of the excitation light,
        n is the refraction index of an optical material in which the intensity distribution of the excitation light with the at least one minimum is formed,
        $\alpha$ is half an aperture angle of an optical arrangement by which the excitation light is directed onto the sample,
        I is a maximum intensity of the excitation light within the sample, and
        $I_s$ is a substance-dependent fluorescence excitation saturation intensity of the excitation light,
    wherein the intensity of the fluorescence light emitted by one of the individual molecules at a location of the local minimum of the intensity distribution of the excitation light is at maximum half as high as the intensity of the fluorescence light emitted by the one of the individual molecules at a location of the maximum intensity of the excitation light within the sample; and
    wherein increments between nearest neighboring positions of the at least one minimum within the sample, in which the fluorescence light from the excited individual molecules of the substance in the fluorescent state is registered, are not greater than half the minimum value d.

2. The method of claim 1, wherein deducing the location of each individual molecule includes fitting a function having a local minimum is fitted to the course of the registered intensity of the fluorescence light over the positions of the at least one minimum in the area of interest of the sample, and wherein the location of the respective molecule is determined as the position of the local minimum of the fitted function.

3. The method of claim 2, wherein the function is a square function.

4. The method of claim 1, wherein deducing the location of each individual molecule includes determining the location of the respective molecule is determined as that position of the at least one minimum in which a lower intensity of the fluorescence light emitted by the respective molecule is registered than in any nearest neighboring position of the minimum within the sample.

5. The method of claim 1, wherein the increments between the nearest neighboring positions of the at least one minimum within the sample, in which the fluorescence light from the excited individual molecules of the substance in the fluorescent state is registered, are not greater than a low excitation area around the minimum, in which one of the individual molecules is only excited for the emission of the fluorescence light at a minimum intensity.

6. The method of claim 1, wherein the intensity of the excitation light adjacent to the at least one minimum is so high that a saturation of the intensity of the fluorescence light is achieved, which is emitted by one of the individual molecules excited by means of the excitation light.

7. The method of claim 1,
    wherein the molecules of the substance are selected from a group of substances which are, by means of an adjusting signal, transferable out of their fluorescent state into a non-fluorescent state or out of a non-fluorescent state into their fluorescent state at a transition probability increasing with the intensity of the adjusting signal;
    wherein, considering all molecules independent on their state, distances between nearest neighboring molecules of the substance in the area of interest of the sample are smaller than the minimum value d; and
    wherein the distances between the individual molecules of the substance in the fluorescent state, which keep the minimum value d, are adjusted by means of the adjusting signal.

8. The method of claim 7,
    wherein the molecules of the substance, in opposite direction to their transfer by means of the adjusting signal, return into their starting state at a further transition probability;
    wherein repeatedly or continuously, at each time for other individual molecules in the fluorescent state, the distances between the individual molecules of the substance in the fluorescent state, which keep the minimum value d, are adjusted by means of the adjusting signal; and
    wherein the locations of the respective individual molecules in the fluorescent state are determined to obtain an image of the distribution of the molecules of the substance within the sample.

9. The method of claim 8, wherein the molecules of the substance return into their starting state driven by a returning signal or spontaneously.

10. The method of claim 8, wherein the sample is subjected to the adjusting signal continuously or intermittently.

11. The method of claim 7, wherein the adjusting signal is adjusting light.

12. The method of claim 11, wherein the molecules of the substance, by means of the adjusting light, are transferred out of their fluorescent state into their non-fluorescent state.

13. The method of claim 12, wherein the non-fluorescent state of the molecules of the substance is an electronic energy state.

14. The method of claim 12, wherein the adjusting light has a same wavelength as the excitation light.

15. The method of claim 1,
wherein the at least one minimum is a point-shaped minimum;
wherein the different positions of the at least one minimum in the area of interest of the sample, in which the fluorescence light from the excited individual molecules of the substance in the fluorescent state is registered, differ in all dimensions of the sample; and
wherein the locations of the individual molecules of the substance in all dimensions of the sample are deduced from the course of the registered intensity of the fluorescence light over the positions of the at least one minimum in the area of interest of the sample.

16. The method of claim 15, wherein the fluorescence light is registered for a registration area including the at least one minimum by means of a point detector confocally arranged with regard to the at least one minimum.

17. The method of claim 1, wherein the at least one minimum extends along a line or a plane, wherein the different positions of the at least one minimum in the area of interest of the sample differ in a scanning direction extending orthogonal to the line or plane, and wherein the locations of the individual molecules of the substance in the scanning direction are deduced from the course of the registered intensity of the fluorescence light over the positions of the at least one minimum in the area of interest of the sample.

18. The method of claim 17, wherein the line or plane is successively oriented in different orientations with regard to the sample to determine the locations of the individual molecules of the substance in different spatial directions.

19. The method of claim 1, wherein the intensity distribution of the excitation light comprises a plurality of minima whose positions in the area of interest of the sample are varied together, wherein the fluorescence light emitted by the excited individual molecules of the substance is separately registered for each of the plurality of minima.

20. The method of claim 1, wherein the fluorescence light is registered by means of a light sensor array which is fixed with regard to the sample.

21. The method of claim 20, wherein frames are continuously read out of the light sensor array and assigned to the respective positions of the at least one minimum within the sample.

22. The method of claim 21, wherein the at least one minimum is continuously moved with regard to the sample.

23. The method of claim 20, wherein the distances of the individual molecules of the substance in the fluorescent state within the area of interest of the sample are greater than the diffraction limit at the wavelength of the fluorescence light, and wherein the locations of the individual molecules of the substance in the fluorescent state are additionally determined from the distribution of the overall fluorescence light emitted by the respective molecule over the light sensor array.

24. An apparatus for determining the locations of individual molecules of a substance in a sample, wherein the individual molecules of the substance are in a fluorescent state in which they are excitable for emission of fluorescence light by means of excitation light, the apparatus comprising
an excitation light source configured to provide the excitation light,
by which the molecules of the substance in the fluorescent state are excited for the emission of the fluorescence light, and
by which the molecules of the substance are transferred out of their fluorescent state into a non-fluorescent state,
light shaping optics configured to form an intensity distribution of the excitation light within the sample which comprises at least one local minimum, wherein the intensity of the fluorescence light emitted by one of the individual molecules at a location of the local minimum of the intensity distribution of the excitation light is at maximum half as high as the intensity of the fluorescence light emitted by the one of the individual molecules at a location of the maximum intensity of the excitation light within the sample;
an optical arrangement configured to project the excitation light into the sample;
a scanning device configured to position the at least one minimum at different positions within the sample; and
a detector device configured to register the fluorescence light emitted by the molecules of the substance in the fluorescent state which have been excited by means of the fluorescence light, wherein the detector device is configured to register the fluorescence light emitted out of a registration area including the at least one minimum separately from fluorescence light emitted out of other areas of the sample;
wherein increments between nearest neighboring positions of the at least one minimum, in which the detector device registers the fluorescence light emitted out of the registration area, are not greater than $\lambda/(4n \sin \alpha \sqrt{(1+I/I_s)})$, wherein
$\lambda$ is a wavelength of the excitation light,
n is the refraction index of an optical material in which the intensity distribution of the excitation light with the at least one minimum is formed by means of the light shaping optics,
$\alpha$ is half the aperture angle of the optical arrangement by which the excitation light is directed into the sample,
I is the maximum intensity of the excitation light within the sample, and
$I_s$ is a substance-dependent fluorescence excitation saturation intensity of the excitation light.

25. The apparatus of claim 24, wherein the light shaping optic forms the intensity distribution of the excitation light within the sample as a grating of local intensity minima, and wherein the scanning device shifts the intensity distribution with regard to the sample such that an area of interest of the sample is completely scanned with low excitation areas around the local intensity minima within which the molecules of the substance in the fluorescent state are only excited for the emission of fluorescence light at a minimum intensity.

26. The apparatus of claim 24, wherein the detector device comprises an image sensor array which is fixed with regard to the sample.

* * * * *